US006358538B1

(12) United States Patent
Provitola

(10) Patent No.: US 6,358,538 B1
(45) Date of Patent: Mar. 19, 2002

(54) METHOD FOR PROTECTING PLANTS FROM FUNGUS

(76) Inventor: Anthony Italo Provitola, P.O. Box 2855, DeLand, FL (US) 32721-2855

( * ) Notice: Subject to any disclaimer, the term of this patent is extended or adjusted under 35 U.S.C. 154(b) by 0 days.

(21) Appl. No.: 09/306,928

(22) Filed: May 7, 1999

(51) Int. Cl.[7] .................. A01N 59/06; A01N 59/00; C05C 1/00; C05C 5/02; C05C 5/04
(52) U.S. Cl. .................. 424/718; 424/682; 71/58; 71/59; 47/DIG. 11
(58) Field of Search .................. 424/718, 682; 71/58, 59; 47/DIG. 11

(56) References Cited

U.S. PATENT DOCUMENTS

| 4,487,783 A | | 12/1984 | Grohe |
| 4,763,440 A | | 8/1988 | James |
| 5,800,837 A | | 9/1998 | Taylor |
| 5,891,908 A | | 4/1999 | Ammermann |
| 6,086,923 A | * | 7/2000 | Stoller .................. 424/678 |

OTHER PUBLICATIONS

Reuveni, M. et al., "Controlling powdery mildew caused by *Sphaerotheca fuliginea* in cucumber by folia sprays of phosphate and potassium salts," Crop Protection, vol. 15(1), Feb. 1996, pp. 49–53.
Mitrokhin, A. N., "Control of wilt in muskmelons," Zashch. Rast., vol. 1, 1974, p. 54.
Chemical Abstracts 81:100578k (1974).
Bhattacharyya, A. et al., "Induction of resistance in rice plant against sheath blight with non–conventional chemicals," Indian Phytopathology, vol. 51(1), 1998, pp. 81–86.
Jenkins, S. F. et al., "Problems and progress in integrated control of southern blight of vegetables," Plant Disease, vol. 70(7), 1986, p. 614–619.*
Lucas, G. B. et al. Introduction to Plant Diseases. The AVI Publishing Co., Wesport, Connecticut, 1985, pp. 18–25 and 141–143.*
Huber, D. M. et al., "Nitrogen form and plant disease" in: Baker, K. F. et al. (eds.), Annual Review of Phytopathology, Annual Reviews Inc., Palo Alto (CA), vol. 12, pp. 139–165, 1974.*
Kumar, R. et al., "Effect of pre–harvest application of fungicide, growth regulators and calcium nitrate on the storage behaviour of perlette grapes at low temperature," Haryana Agricultural University Journal of Research, vol. 17(1), pp. 30–38, 1987.*
Barker, A. V. et al., "Growth and composition of tomato as affected by source of nitrogen and biocides," Journal of Plant Nutrition, vol. 12(1), pp. 95–109, 1989.*

* cited by examiner

Primary Examiner—John Pak

(57) ABSTRACT

A method for protecting a ground plot of plants, a hydroponic system of plants, and the like from fungal infection by the application of a solution of nitrates to the plants, ground surface and other associated structures present on which fungus spores may be located in order to inhibit fungus spore germination upon the occurrence of conditions of darkness and humidity favorable therefor.

18 Claims, No Drawings

METHOD FOR PROTECTING PLANTS FROM FUNGUS

CROSS-REFERENCE TO RELATED APPLICATIONS

None

STATEMENT REGARDING FEDERALLY SPONSORED RESEARCH OR DEVELOPMENT

Not Applicable

REFERENCE TO MICROFICHE APPENDIX

Not Applicable

BACKGROUND OF THE INVENTION

The present invention is a method for protecting a ground plot, or hydroponic system, or any growing arrangement of plants from fungal infection, and for inhibiting the growth of fungus in the environment on the atmospherically exposed surfaces of the plants. It has been found by experiment that weak solutions of nitrates are an unfavorable environment for the germination of fungal spores and for their subsequent development. It appears that the dissociated nitrate ion has a fungistatic effect, which has been found to occur under certain conditions using various fertilizer quality nitrate salts. The effect extends to fungi on the ground surface as well as on the plant surfaces.

The present invention does not build on any prior art utilizing the effect of nitrates on fungal spore germination in the field of plant husbandry. However, its well known that nitrate salts are effective food preservatives, especially with respect to combating spoilage, the chief agent of which are fungi. The application of this effect to plant husbandry must take into account the fungal reproductive mechanism to provide the inhibitor when conditions favor germination of fungus spores. The fungistatic effect of nitrates has not been employed in the agricultural community, as evidenced by the growing dependence on complex commercial fungicides designed to create a toxic environment for fungus. Unfortunately, such fungicides also negatively impact the environment of other species as well.

It is also well known that fungal propagation, and thus fungal infection of plants, occurs in darkness and requires the presence of some moisture at a proper temperature. Such conditions establish the point of opportunity for the effectiveness of the present invention.

The process of fertilization with nitrate salts by injection of dissolved salts into irrigation water during distribution to plants, known as fertigation, is widely practiced, as is the practice of injecting pesticides into irrigation water during distribution to plants, known as chemigation. The use of the irrigation system for distribution of a nitrate solution is the tool of the present invention, and is employed by the preferred embodiment.

With respect to the field of the use of fertilizer materials to attack fungal parasitism U.S. Pat. No. 5,800,837, entitled Plant Fertilizer Compositions Containing Phosphate and Phosphate Salts and Derivatives Thereof, provides an adequate history, but only claims an invention related to the effect of the fertilizer composition in eliminating an obstacle to the operation of phosphonate-based fungicide. Also fairly recently U.S. Pat. No. 5,891,908, Fungicidal Mixtures, directly addresses the problem of fungal infection of plants, but only offers combinations of commercially known carbamate fungicides. Both of these patents are of value here, however, in understanding the state of the art.

The present invention is covered generally by class/subclass 47/2, 26,27; 514/491, 476, 528, 539; 424/322, 601.

BRIEF SUMMARY OF THE INVENTION

The present invention is a method for protecting a ground plot of plants or a hydroponic system of plants and the like from fungal infection and for inhibiting the growth of fungus in the environment on the atmospherically exposed surfaces of the plants, thereby preventing fungal infection and consequent damage to the plants. The method comprises the principal step of delivering a solution containing nitrate salts as the only solute into the environment of the plants, so that all vulnerable atmospherically exposed surfaces of the plants receive a film of such nitrate solution.

It is the object of the present invention to alter the environment on and about the atmospherically exposed surfaces of plants so that germination of fungal spores will be inhibited, and thus to prevent fungal infection of the plants through such plant surfaces.

The present invention can be used with an irrigation system that can deliver water to the plants in the form of water droplets through sprinklers and/or mist heads. Such an irrigation system may thus also be used to deliver the nitrate solution by timely injection into the irrigation flow. When the foliage of the plants is dense other methods of delivery of the nitrate solution may be used. The method which is the present invention also incorporates certain rules, which take into consideration conditions of moisture and darkness to which the plants are regularly subject, according to which the nitrate solution is to be applied to be effective.

BRIEF DESCRIPTION OF THE DRAWINGS

No Drawings

DETAILED DESCRIPTION OF THE INVENTION

The present invention is a method for protecting a ground plot or hydroponic system of plants, and the like, from fungal infection through the atmospherically exposed surfaces of plants and for inhibiting the growth of fungus in the environment of the atmospherically exposed surfaces of plants, thereby preventing fungal infection through such surfaces and consequent damage to the plants.

It is well known that fungus spores are ubiquitous in the atmospheric environment, and that such entities are virtually indestructible under normal agricultural growing conditions. Therefore, the only way to attack fungal infection of plants is to destroy the fungus in its early development, or to inhibit the germination of its spores. It is the object of the present invention to alter the environment on and about the atmospherically exposed surfaces of plants so that germination of fungal spores will be inhibited, and thus to prevent fungal infection of the plants through such surfaces. It is also an object of the present invention to provide a method which is useable in warm climates with frequently high humidity so that crops susceptible to fungi favored by such conditions may be grown without the use of fungicides. Such an alternative to fungicides is important in areas where the agricultural industry for such a crop is not significantly large to make it economically feasible for fungicide producers to seek the environmental protection certification necessary for its use on the crop in that area, and where the plants are particularly susceptible to certain localized strains of fungus for which no effective fungicides are labeled for use. More importantly, the present invention reduces the complex chemical load on the environment while providing for direct crop nutrition with nitrates by surface absorption, a more efficient use of nitrates than soil borne solutions and solid distributions.

It has been found by experiment that weak solutions of nitrates are an unfavorable environment for the germination of fungal spores, and possibly also for subsequent development after germination. It thus appears that the dissociated nitrate ion has a fungistatic effect, which has been found to occur under certain conditions using various fertilizer quality nitrate salts. The effect extends to fungi on the ground surface as well as on the plant surfaces. No tests were made to determine the effect on subterranean fungus, but no adverse fungal infections were observed over the test period. Moreover, certain species of subterranean fungi are beneficial to the health of the plants, and it would be counterproductive to interfere in such symbiotic processes.

The method which is the present invention is based upon the above-mentioned experimental finding, and comprises the principal step of delivering a solution containing nitrate salts as the only solute into the environment of the atmospherically exposed surfaces of plants, at certain times and under certain conditions, so that all vulnerable atmospherically exposed surfaces of the plants receive a film of such nitrate solution. Various fertilizer quality nitrate salts have been used to test this effect, particularly potassium nitrate, ammonium nitrate, calcium nitrate, and sodium nitrate. The nitrate salts also serve as plant nutrients when they are ultimately washed into the soil. The concentration of nitrate ions in the solution at the sprinkler/mist head which has been found to be generally effective for plants in open ground plots is 700 parts per million of water, but such concentration may be altered as necessary to suit the method and conditions of application. That concentration was achieved by the application of approximately 10 pounds of nitrate salts for application to each acre dissolved in approximately 1,000 gallons of water. For distribution of sufficient amounts of nitrate ions to the surfaces of plants in ground plots with heavy foliage as much as 20 pounds of nitrate salts per acre or more in the same amount of water may be necessary. The time rate of distribution through an irrigation system by sprinklers for plants in open ground plots, of a solution in which the concentration of nitrate ions is 700 parts per million of water by weight at the sprinkler, should be approximately 1,000 gallons per acre uniformly over a period of approximately 5 minutes. For application to plant plots and hydroponic systems through mist heads, the concentration should be increased in direct proportion to the decrease necessary in the total volume of the solution applied, with care being taken to provide coverage for all of the plant material to be treated over the period of application. The period of application may also be lengthened or shortened with appropriately proportional changes in the other parameters, with the caution that the shorter the period, the more difficult it is to obtain adequate coverage. The use of a means of delivery of nitrate solution to the plants, including sprinkler/mist heads, should be directed to providing equivalent levels of nitrate ion concentration on plant surfaces as the concentration of nitrate solution found to be effective as stated herein.

The present invention can be used with an irrigation system that can deliver water to the plants in the form of water droplets through sprinklers and/or mist heads. Such an irrigation system may also be used to deliver the nitrate solution by timely injection into the irrigation flow. When the foliage of the plants is dense other methods of delivery of the nitrate solution may be used, including blower-spraying. For surface grown bulb-type crops, such as onions, a sprinkler system with good distribution is adequate. For crops having dense foliage, including decorative foliage types, it will be necessary to create a mist of the nitrate solution that penetrates to all of the foliage. Surfactants can be used to assist in the distribution of the nitrate ions upon contact of water or mist droplets with the plant. Such a misting system can also be a part of the irrigation system equipped with a fertilizer injection system.

The method which is the present invention includes a system of rules which take into consideration conditions of moisture and darkness to which the plants are regularly subject, and according to which the nitrate solution is to be applied to be effective. These rules are as follows:

1. Application of the nitrate solution should be made at least every other day for dense foliage and at least once every three days for plant plots.

2. The nitrate salts used for the application should be the only compounds dissolved in the water other than background impurities.

3. Once the nitrate solution is applied, the plants or associated structures should not be disturbed by physical contact of any kind initiated by human beings or machines, such as walking through the plants or spraying other chemicals.

4. Application of the solution of nitrates should be made immediately at sunset or upon the onset of other low-light conditions on days during which it has rained or irrigation has taken place.

5. If rain lasts into darkness, periodic application of the solution of nitrates should be made at approximately two-hour intervals commencing with sunset or other low-light conditions, with the last application immediately after the cessation of the rain.

6. Fertilization with nitrates should be reserved for use as indicated in rules 1, 4 and 5.

7. For plant plots to which the nitrate solution is applied through the irrigation system by sprinklers the concentration of nitrate ions should be at least 500 parts per million of water by weight at the sprinkler at a rate of approximately 1,000 gallons per acre uniformly over a period of approximately 5 minutes. For application to plant plots and hydroponic systems through mist heads, the concentration should be increased in direct proportion to the decrease necessary in the total volume of the solution applied, with care being taken to provide coverage for all of the plant material to be treated over the period of application. The period of application may also be lengthened or shortened with appropriately proportional changes in the other parameters, with the caution that the shorter the period, the more difficult it is to attain adequate coverage.

The object of the foregoing rules is to provide a sufficient film of nitrate salts on the atmospherically exposed plant surfaces that can ionize in dew or other conditions of high humidity during periods between applications so that fungistatically effective amount of nitrate ions in aqueous solution is present on such surfaces. Even without rain or irrigation such a film of nitrate salts will be diminished by direct absorption by the plant surfaces as well as effects such as drippage and evaporation. Therefore, conditions of heat and low humidity should be taken into account in decisions regarding frequency of application of nitrate solution to the atmospherically exposed surfaces of the plants.

The use of this method or system should not be augmented or combined with the use of commercial fungicides on the atmospherically exposed surfaces of the plants. It is thought that the application of commercial fungicides which do not completely eliminate all genetic strains favor those which are most resistant to the fungicide by eliminating the population of the weaker strains. Such a change in the fungus population may also genetically select those strains whose spore germination and development is not as inhibited by the presence of nitrates in the environment.

Under ordinary circumstances there will be a minimum infection level in areas where adequate distribution of nitrate solution does not take place. However, this occurs only as a result of the localized absence of nitrate solution or its untimely delivery to such an area, because of physical factors that can alter the delivery system, such as wind, malfunction of equipment, clogging of sprinklers or mist heads, etc. The effect of the method which is the present invention may be optimized if care is taken to properly distribute the nitrate solution to the atmospherically exposed surfaces of the plants and associated structures, including agitation of the misted atmosphere about the plants, filtering fluid flows to sprinkler and mist heads to avoid clogging thereof, and avoidance of other distribution anomalies.

Transition to the use of the present invention from the use of commercial fungicides requires a period of disuse of such fungicides, such as with new plantings, during periods of plant dormancy, or other conditions where fungus spores are not likely to germinate.

While the invention has been disclosed in connection with a preferred embodiment, it will be understood that there is no intention to limit the invention to the particular embodiment shown, but it is intended to cover the various alternative and equivalent constructions included within the spirit and scope of the appended claims.

What I claim as my invention is:

1. A method for protecting plants from fungal infection comprising applying an aqueous solution containing at least 500 parts of nitrate salts per million parts of water, by weight, to all atmospherically exposed surfaces of plants and associated structures, so that fungal spores which are present on said surfaces are subjected to an environment comprising a fungistatically effective amount of nitrate ions in the aqueous solution, wherein:
   (i) application of the aqueous solution is made at least once every three days;
   (ii) application of the aqueous solution is made immediately upon the onset of low-light conditions on days during which it has rained or irrigation has taken place;
   (iii) periodic application of the aqueous solution is made at approximately two-hour intervals when rain lasts into darkness, commencing with low-light conditions;
   (iv) the last application of the aqueous solution is immediately after the cessation of rain; and
   (v) the aqueous solution is uniformly applied at a rate of approximately 1,00 gallons per acre over a period of approximately 5 minutes.

2. The method of claim 1, wherein the aqueous solution consists essentially of nitrate salts, a surfactant and water.

3. The method of claim 1, wherein the nitrate salts are selected from the group consisting of potassium nitrate, calcium nitrate and sodium nitrate.

4. A method of reducing fungal infection through the atmospherically exposed surfaces of plot plants and plants in hydroponic systems comprising subjecting fungal spores which are present on said surfaces to an environment comprising a fungistatically effective amount of nitrate ions in aqueous solution, wherein (i) said subjecting step comprises applying a fungistatically effective amount of nitrate ions in aqueous solution to fungal spores on said surfaces, and
(ii) additionally applying a fungistatically effective amount of nitrate ions in aqueous solution at approximately two-hour intervals when rain lasts into darkness, commencing with the onset of low-light conditions during rain, with the last application being immediately after the cessation of rain.

5. The method of claim 4, wherein part (i) is carried out at least once every three days.

6. The method of claim 4, wherein part (i) or part (ii) is the last machine or human initiated physical contact of any kind with the plants until dawn of the next day.

7. The method of claim 4, wherein part (i) is carried out immediately upon the onset of low-light conditions on days during which it has rained or irrigation has taken place.

8. The method of claim 4, wherein the rate of application of the nitrate ions is an amount of nitrate ions in at least 10 pounds of nitrate salts per acre.

9. The method of claim 4, wherein the rate of application of the nitrate ions in aqueous solution is approximately 1,000 gallons per acre uniformly distributed over a period of approximately 5 minutes.

10. The method of claim 4, wherein the source of the nitrate ions is a nitrate salt selected from the group consisting of potassium nitrate, calcium nitrate and sodium nitrate.

11. The method of claim 4, wherein the fungistatically effective amount of nitrate ions in aqueous solution is delivered by an aqueous solution consisting essentially of nitrate salts, a surfactant and water.

12. The method of claim 11, wherein the concentration of the nitrate ions in aqueous solution is at least 500 parts per million by weight.

13. The method of claim 12, wherein the rate of application of the nitrate ions in aqueous solution is approximately 1,000 gallons per acre uniformly distributed over a period of approximately 5 minutes.

14. The method of claim 12, wherein the concentration of the nitrate ions in aqueous solution is increased in compensation for a decrease in the total volume of the solution applied.

15. A method for protecting plants from fungal infection, said method comprising the steps of:
   providing a means of delivery of droplets of an aqueous solution of nitrate salts to atmospherically exposed surfaces of plants;
   applying an aqueous solution of nitrate salts with a concentration of nitrates of at least 500 parts per million by weight to atmospherically exposed surfaces of plants and associated structures by said means of delivery in accordance with the following system:
      (i) application of the aqueous solution is made at least once every three days;
      (ii) application of the aqueous solution is made immediately upon the onset of low-light conditions on days during which it has rained or irrigation has taken place; and
      (iii) periodic application of the aqueous solution is made at approximately two-hour intervals when rain lasts into darkness, commencing with low-light conditions, with the last application being immediately after the cessation of rain;
so that fungal spores which are present on said surfaces are subjected to an environment comprising a fungistatically effective amount of nitrate ions in aqueous solution.

16. The method of claim 15, wherein the rate of application of the aqueous solution is approximately 1,000 gallons per acre uniformly distributed over a period of approximately 5minutes.

17. The method of claim 15, wherein the aqueous solution consists essentially of nitrate salts, a surfactant and water.

18. The method of claim 15, wherein the nitrate salts are selected from the group consisting of potassium nitrate, calcium nitrate and sodium nitrate.

* * * * *